US005633000A

United States Patent [19]
Grossman et al.

[11] Patent Number: 5,633,000
[45] Date of Patent: May 27, 1997

[54] SUBCUTANEOUS IMPLANT

[75] Inventors: Stuart A. Grossman, Towson; Kam W. Leong, Ellicott City; Glenn J. Lesser; Hungnan Lo, both of Baltimore, all of Md.

[73] Assignee: Axxia Technologies, Bethesda, Md.

[21] Appl. No.: 264,689

[22] Filed: Jun. 23, 1994

[51] Int. Cl.$^6$ .............................. A61K 9/00; A61K 9/22; A61K 9/24
[52] U.S. Cl. .................. 424/422; 424/423; 424/424; 424/425; 424/468; 424/473; 424/486
[58] Field of Search .................... 424/423, 424, 424/425, 468, 473, 486, 422

[56] References Cited

U.S. PATENT DOCUMENTS 4,863,736   9/1989   Azain et al. ............................ 424/423

OTHER PUBLICATIONS

Joranson, D.E., Journal of Pain and Symptom Management, vol. , No. 6, pp. 353–360, Aug. 1993, "Availability of Opioids for Cancer Pain: Recent Trends, Assessment of System Barriers, New World Health Organization Guidelines, and the Risk of Diversion".
Rhine, W.D., et al, Journal of Pharmaceutical Sciences, vol. 69, No. 3, pp. 265–270, Mar. 1980, "Polymers for Sustained Macromolecule Release: Procedures to Fabricate Reproducible Delivery Systems and Control Release Kinetics".
Joranson, D.E., Journal of Pain and Symptom Management, vol. , No. 6, pp. 353–360, Aug. 1993, "Availability of Opioids for Cancer Pain: Recent Trends, Assessment of System Barriers, New World Health Organization Guidelines, and the Risk of Diversion".
Sefton, M.V., et al, Journal of Pharmaceutical Sciences, vol. 73, No. 12, pp. 1859–1861, Dec. 1984, "Ethylene–Vinyl Acetate Copolymer Microspheres for Controlled Release of Macromolecules".
Cohen, J., et al, Journal of Pharmaceutical Sciences, vol. 73, No. 8, pp. 1034–1037, Aug. 1984, "Sintering Technique for the Preparation of Polymer Matrices for the Controlled Release of Macromolecules".
Kuu, Wei–Youh, et al, Journal of Pharmaceutical Sciences, vol. 74, No. 9, pp. 926–933, Sep. 1985, "Multiple–Hole Approach to Zero–Order Release".
Miyazaki, S., et al, Chem. Pharm. Bull., 29(9) 2714–2717 (1981) "Controlled Release of prednisolone from Ethylene–Vinyl Acetate Copolymer Matrix".
Wyszynski, R.E., et al, Journal of Ocular Pharmacology, vol. 5, N. 2, pp. 141–146 (1989). "Sustained Release of 5–Fluorouracil from Ethylene Acetate Copolymer".
Lin S.Y., et al, Biomat., Art. Cells, Art. Org., 17(2), 189–203 (1989), "Tumoricidal Effect of Controlled–Release Polymeric Needle Devices Containing Adriamycin HCl in Tumor–Bearing Mice".
Brown, L., et al, Diabetes, vol. 35, pp. 692–697, Jun. 1986, "Controlled Release of Insulin From Polymer Matrices".
Hoffman, D., et al, Experimental Neurology 110, 39–44 (1990), "NGF Released from a Polymer Matix Prevents Loss of ChAT Expression in Basal Forebrain Neurons following a Fimbria–Fornix Lesion".

Radomsky, M.L., et al, Biomaterials, vol. 11,619–24 (1990) "Macromolecules Released From PolymersL Diffusion into Unstirred Fluids.".
Niemi, S.M., et al, Laboratory Animal Science, vol. 35, No. 6, 609–612, Dec. 1985, "Evaulation of Ethylene–Vinyl Acetate Copolymer as a Non–Inflammatory Alternative to Freund's Complete Adjuvant in Rabbits".
During, M.J., et al, Annals of Neurology, vol. 25, No. 4, pp. 351–356, Apr. 1989, "Controlled Release of Dopamine from a Polymeric Brain Implant: In Vivo Characterization".
Sabel, B.A., et al, Annals of Neurology, vol. 28, No. 5, pp. 714–717, Nov. 1990, "Extended Levodopa Release from a Subcutaneously Implanted Polymer Matrix in Rats".
Brown, L.R., et al, Journal of Pharmaceutical Sciences, vol. 72, No. 10, pp. 1181–1185, Oct. 1983, "In Vivo and In Vitro Release of Macromolecules from Polymeric Drug Delivery Systems".
Langer, R., et al, Journal of Biomedical Materials Research, vol. 15, 267–277 (1981) "Biocompatibility of Polymeric Delivery Systems for Macromolecules".
Brook, I.M., et a., British Dental Journal, 157:11 Jul. 7, 1984, "Controlled Delivery of Drugs".
Hsieh, D.S.T., et al, Journal of Pharmaceutical Sciences, vol. 72, No. 1, pp. 17–22, Jan. 1983, "Zero–Order Controlled–Release Polymer Matrices for Micro– and Macromolecules".
Grossman, S.A. et al, Proceedings of ASCO, vol. 10, p. 337, Mar. 1991, "A Non–Abusable parenteral Narcotic Delivery System for Continuous Subcutaneous (SQ) Administration".
Vallner, J.J., et al, J. Clin. Pharmacol., 21:152–156 1981; "Pharmacokinetics and Bioavailability of Hydromorphone Following Intravenous and Oral Administration to Human Subjects".
Bruera, E., et al, Journal of the National Cancer Institute, 80:1152–1154 (1988), "Patient–Controlled Subcutaneous Hydromorphone Versus Continuous Subcutaneous Infusion for the Treatment of Cancer Pain".
Reidenberg, M.M., et al, Clin. Pharmacol. Ther., 44:376–82 (1988) "Hydromorphone Levels and Pain Control in Patients with Severe Chronic Pain".
Moulin, D.E., et al, Can. Med. Assoc. J., 146(6) 891–898, Mar. 15, 1992, "Subcutaneous Narcotic Infusions for Cancer Pain: Treatment Outcome and Guidelines for Use".
Moulin, D.E., et al, Lancet, 337:465–68, Feb. 23, 1991, "Comparison of Continuous Subcutaneous and Intraveous Hydromorphone Infusions for Management of Cancer Pain."
Strain, E.C., et al, Annals of Internal Medicine, vol. 119, No. 1, pp. 23–27, Jul. 1, 1993, "Dose–Response Effects of Methadone in the Treatment of Opioid Dependence".
Gerstein, D.R., The New England Journal of Medicine, pp. 844–848, Sep. 20, 1990, "Treating Drug Problems".
Brown, L., et al. Diabetes, vol. 35, pp. 684–691, Jun. 1986 "Controlled Release of Insulin from Polymer Matrices".

*Primary Examiner*—Jeffrey C. Mullis
*Attorney, Agent, or Firm*—Nixon & Vanderhye P.C.

[57] ABSTRACT

A non-abusable, non-inflammatory, biocompatible, non-biodegradable, subcutaneous, polymeric implant for the prolonged, controlled release of hydromorphone with near zero-order kinetics is described. Methods of alleviating cancer pain and treating opioid drug addiction with the implant are also described.

15 Claims, 10 Drawing Sheets

SUBCUTANEOUS IMPLANT

FIELD OF THE INVENTION

This invention relates to a unique device for the chronic subcutaneous administration of a potent opioid in a form that renders it difficult to divert for illicit use and ensures prolonged steady release of this agent, thereby providing long term pain relief or treatment of opioid drug addiction, and preventing the potentially lethal consequences of an uneven release of drug from the device.

BACKGROUND OF THE INVENTION

Approximately 70% of patients with cancer experience pain attributable to their neoplasm or its therapy. As life expectancy has increased in developed and developing countries, cancer and cancer-related pain have become major social and medical concerns. The worldwide availability of opioid analgesics, the primary therapy for most cancer-related pain, varies greatly. In 1991, 20 developed countries accounted for 86% of the morphine consumed in the world while the remaining 14% of morphine was consumed in the remaining countries having the majority of the world's population. (Joranson, D. E., *Journal of Pain and Symptom Management*, 8(6): 353–360, 1993).

The scant use of opiates for the relief of cancer pain for the majority of the world's population is a result of many factors including concerns over drug diversion for illicit use and addiction. Further, many patients with cancer-related pain require long-term continuous dosing of opioid analgesics which often necessitates the ingestion of multiple pills or tablets many times a day. Compliance with this dosing scheme is often poor. Further, enteral drug delivery is poorly tolerated or prohibited in many patients with cancer-related pain in whom continuous drug delivery is a necessity. However, continuous parenteral delivery of opioid analgesics is expensive, cumbersome, and dependent upon the availability of refrigeration, catheters, pumps and trained personnel.

Drug addiction is a major societal problem throughout the world. In the United States alone, on any given day, there are several hundred thousand addicts who are enrolled in treatment clinics. Most of them are placed on "methadone maintenance" as a basic part of their therapy. Major behavioral and compliance problems commonly complicate treatment.

The cost of "methadone maintenance" therapy is several hundred dollars per month per patient. A significant portion of this cost relates to the frequent clinic visits and the monitoring of urine tests that are run to assure proper compliance with drug dosing, as well as the pharmacy charges relating to methadone dispensing.

Delivery systems and devices for controlled release of drugs; i.e., controlled release and sustained or prolonged release, are well known in the art. A variety of methods have been described in the literature, including the physiological modification of absorption or excretion, modification of the solvent, chemical modification of the drug, absorption of drug on an insoluble carrier, use of suspensions and implantation pellets. Other methods include mixing the drug with a carrier such as waxes, oils, fats, and soluble polymers which are gradually disintegrated by the environment resulting in release of the drug. Much attention has been directed to the reservoir type of device, i.e., a device in which a drug is encased within a polymeric container, with or without a solvent or carrier, which allows passage of drug from the reservoir.

Another type of drug delivery device is the monolithic type in which a drug is dispersed in a polymer and from which the drug is released by degradation of the polymer and/or by passage of the drug through the polymer. Ethylene-vinyl acetate (EVA) copolymer is a well known representative of an imperforate polymer (Rhine, WD, et al, *Journal of Pharmaceutical Sciences* 69: 265–270, 1980; Sefton, M. V., et al, *Journal of Pharmaceutical Sciences*, 73: 1859–1861, 1984; Cohen, J., et al, *J. Pharm. Sci.*, 73: 1034–7, 1973). The release kinetics of a drug from a polymeric delivery system are a function of the agent's molecular weight, lipid solubility, and charge as well as the characteristics of the polymer, the percent drug loading, and the characteristics of any matrix coating. The importance of these factors coupled with the specific pharmacology, toxicology, and therapeutic goals necessitate that the design of a polymeric implant for a specific agent must be carefully constructed.

Ku et al, *J. Pharm. Sci.*, 74, p.926 (1985) describe a multiple-hole approach to obtain zero order release.

The sustained parenteral delivery of opioid antagonism and agonists has been an area of considerable interest because first, it may afford a new approach to the treatment of opioid drug abuse and second, the undertreatment of pain is widely recognized throughout the world.

A. Narcotic Antagonist: Naltrexone

Over the past two decades, a variety of approaches have been attempted using polymers containing narcotic antagonists in an effort to prevent drug abuse. The release characteristics of these antagonists are less critical than those of the pure agonists as evidenced by the first-order kinetics noted in the literature.
1. Glycerine implants
2. Cholesterol-glyceryltriesterate demonstrated first order kinetics in rats
3. Glutamic acid and leucine—biodegradable
4. Polylactic/glycolic acid (PLGA) beads B. Narcotic Mixed Agonist/Antagonist: Buprenorphine First order kinetic release using an agent which is not preferred for the treatment of chronic pain.
1. Cholesterol-glyceryltriesterate demonstrated first order kinetics in rats.

C. Narcotic Agonist: Morphine

Morphine is an excellent agent for the treatment of pain but is seven times less potent than hydromorphone and thus, is much less suitable for long-term subcutaneous implant. Many of these implants have demonstrated first-order kinetic release which would threaten the lives of patients receiving implants containing lethal amounts of opioids.
1. Polymeric silicone elastomer
2. Silicone with sodium alginate (swells on contact with water to release drug)
3. Pellets
4. Polyanhydride formulation D. EVA Implants EVA (ethylene vinyl acetate) polymers have been used to deliver many classes of drugs: Hormones (i.e., prednisolone, insulin), antineoplastic agents (i.e., 5FU, adriamycin), proteins (i.e., albumin, immunoglobulins), neurotransmitters (i.e., dopamine), and antibiotics. A burst of these agents is inconsequential compared to a burst of potent opioids.
1. Prednisolone (Miyazaki, S., et al, *Chem. Pharm. Bull* (Tokyo), 29: 2714–7, 1981
2. 5FU (Wyszynski, R. E., et al, *J. Ocul. Pharmacol.*, 5: 141–6, 1989)
3. Adriamycin (Lin, S. Y., et al, *Biomat Art Cells Art Org.*, 17: 189–203, 1989.

4. Insulin (Brown, L., et al, *Diabetes*, 35: 692–7, 1986; Brown, L., et al, *Diabetes*, 35: 684–91, 1986)—EVA coated and with hole in one face of the polymer giving near constant release rates.
5. Nerve Growth Factor (Hofman, D., et al, *Bxp Neurol*, 110: 39–44, 1990)
6. Immunoglobulin (Radomsky, M. L., et al, *Biomaterials*, 11: 619–24, 1990)
7. Albumin (Niemi, S. M., et al, *Lab Anita. Sci.*, 35: 609–12, 1985)
8. Dopamine/Levodopa (During, M. J., et al, *Ann. Neurol.*, 25: 351–356, 1989; Sabel, B. A., et al, *Ann. Neurol.*, 28: 714–717, 1990)

Mechanisms for making EVA polymers and tests of their biocompatibility and non-inflammatory nature have been described in the literature. Brown, L. R., et al, *J. Pharm. Sci.*, 72: 1181–5, 1983; Langer, R., et al, *J. Biomed. Mater. Res.*, 15: 267–77, 1981; and Niemi, S. M., et al, *Lab. Anim. Sci.*, 35: 609–12, 1985, all describe the non-inflammatory nature of the polymer and techniques for polymer manufacture.

Critical factors involved in changing the release characteristics of drugs from EVA polymer have been described (Brook, I. M., et al, *Br. Den. J.*, 157: 11–15, 1984).

U.S. Pat. No. 5,153,002, hereby incorporated by reference, describes a cube with 5 sides coated with impermeable layer and a cylinder with all but one flat side coated. A hemisphere with impermeable coating (paraffin) except for exposed cavity in the center face provides zero order kinetics for albumin release (Hsieh, D. S., et al, *J. Pharm. Sci.*, 72: 17–22, 1982). EVA with impermeable coating of polymer with hole in the center of one face provides zero order kinetics for insulin release. Drug particle size, drug loading, and matrix coating all significantly affect release kinetics (Rhine, W. D., et al, *J. Pharm. Sci.*, 69: 265–70, 1980).

Grossman et al (*Proceedings ASCO*, Vol. 19, p337 (1991)) describe a delivery system where hydromorphone was embedded into a controlled release matrix made of poly-[ethylene-vinyl acetate].

OBJECTS OF THE INVENTION

It is an object of the invention to provide an implantable, biocompatible polymer that continuously delivers a stable concentration of an opioid analgesic subcutaneously for periods ranging from two weeks to in excess of six months.

It is a further object of the invention to provide a means to administer the pain reliever hydromorphone in a form which makes it difficult to divert for illicit use.

SUMMARY OF THE INVENTION

The subject invention relates to a subcutaneous delivery system comprising: i) a polymeric matrix material, ii) a therapeutic agent embedded in said matrix, and, iii) a coating surrounding said matrix, wherein said delivery system is adapted to provide near constant delivery of hydromorphone.

The invention also includes a method of providing a delivery system comprising i) implanting a therapeutic agent in a polyethylene vinyl acetate matrix, ii) forming said matrix into a cylinder, iii) coating said matrix with poly (methyl methacrylate), and iv) creating a cylindrical opening along the axis of the cylindrical matrix creating an internal wall in said matrix, wherein said internal wall of said matrix has no coating.

The invention also involves a method of providing prolonged relief of pain in a mammal suffering from pain comprising subcutaneously administering at least one device (where two or more are administered, they are joined together or separate) to said mammal, and further involves a method of treating opioid drug addiction in a mammal having such an addiction comprising subcutaneously administering at least one device to said mammal.

DETAILED DESCRIPTION OF THE INVENTION

Figure 1:
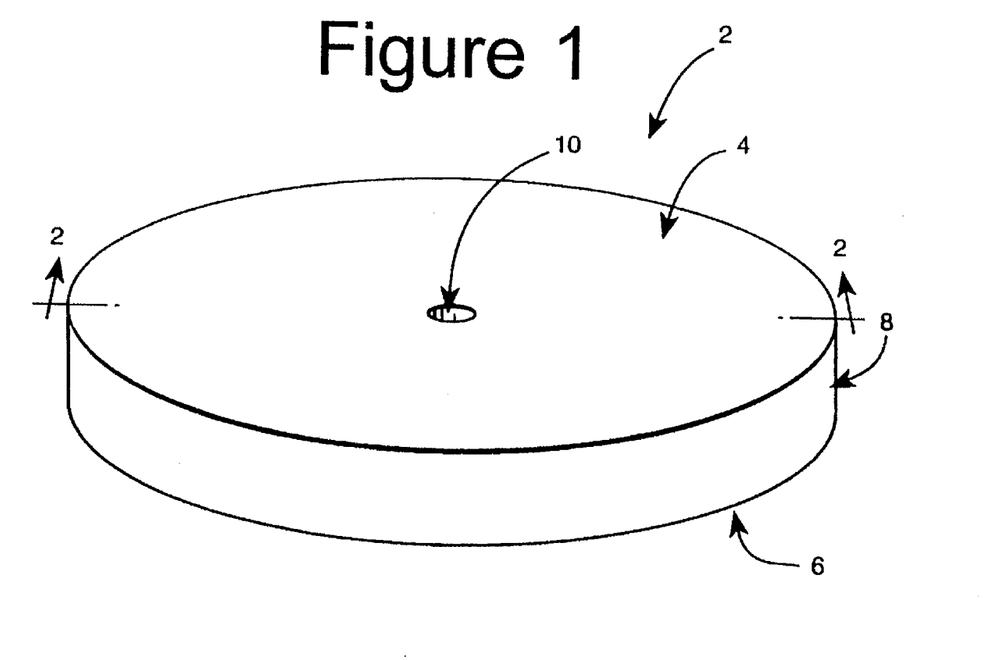
FIG. 1 is a perspective view of a delivery device according to the invention.
Figure 2:
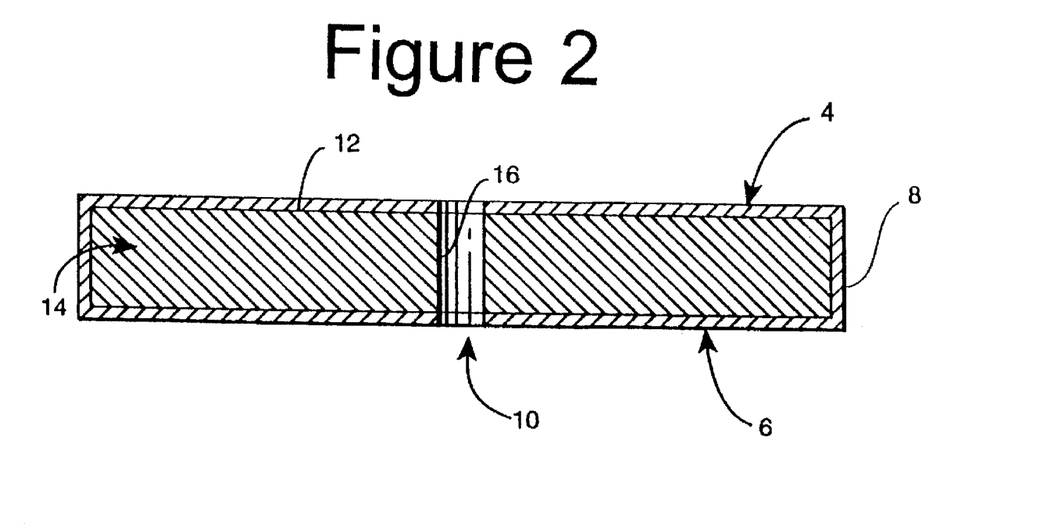
FIG. 2 is a cross-sectional view of a delivery device taken along line 2—2 of FIG. 1. The thickness of the coating has been exaggerated for illustrative purposes.

The subject invention relates to a biocompatible, non-inflammatory, and non-biodegradable implant device 2 which permits controlled release of a potent opioid by subcutaneous implant. A drug such as hydromorphone is imbedded in a controlled release matrix 14 such as polyethylene-vinyl acetate, and this polymer is coated with the biocompatible and hydromorphone impermeable polymer 12 such as poly(methyl methacrylate). The implant typically has a cylindrical geometry with a diameter of the top 4 and bottom 6 of the cylinder, greatly exceeding height of the outside wall 8 of the cylinder. The implant 2 is perforated creating an opening 10 in the top 4 and bottom 6 of the device 2 and creating an uncoated internal cylindrical wall 16. This structure permits steady release of hydromorphone.

The delivery device of the invention minimizes the opportunity for drug diversion, improves compliance, and eliminates the need for expensive support personnel and equipment, and the need for expensive and often unavailable external catheters and pumps in patients with cancer-related pain who require continuous opiate administration. The device delivers stable amounts of hydromorphone in vitro and in vivo for prolonged periods of time. The plasma hydromorphone levels achieved by the subject invention produce no significant toxicity. The steady levels achieved reduce toxicity and improve efficacy. The plasma hydromorphone levels and the variability in those levels achieved with implants is quite similar to the values obtained with osmotic pumps.

The coating 12 of the EVA polymer containing drug effectively eliminates the initial "burst" of drug release seen with many other delivery devices. Unlike intravenous bolus administration, the plasma hydromorphone levels obtained after device implantation remain stable and within the therapeutic range for the entire dosing interval.

Variations in the thickness (i.e., height of wall 8) and diameter (i.e., diameter of top 4 and bottom 6) of these devices as well as in the number of devices implanted provides flexibility in the amount of hydromorphone released per hour, and duration of hydromorphone release, and the magnitude of the plasma hydromorphone levels obtained.

The subject invention solves the problem of the "burst effect" for hydromorphone, eliminates repeated injections of hydromorphone, provides a longer term management for stable and/or chronic cancer pain, provides a means to treat opioid drug addiction, and prevents abuse of the narcotic, i.e., drug diversion, since the technology makes it extremely difficult to extract the hydromorphone from the device of the invention.

The Opioid

Hydromorphone (including hydromorphone hydrochloride) is a water soluble, potent (6–7 times more potent than morphine) opioid approved for subcutaneous use and commonly administered to patients with cancer-related pain. Vallner et al, *J. Clin. Pharmacol* 21: 152–6, 1981, Bruera et al, *J. Natl. Cancer Inst.*, 80: 1152–4, 1988, Reidenberg et al, *Clin. Pharmacol Ther.*, 44: 376–182, 1988, Moulin et al, *Can. Med. Assoc. J.*, 146: 891–7, 1992, Moulin et al, *Lancet*, 337: 465–8, 1991. Constraints on the size of a subcutaneous delivery device favor the use of this opioid. Hydromorphone has excellent water solubility and gives favorable pattern of release from hydrophobic EVA polymer.

The Matrix

Ethylene vinyl acetate (EVA) copolymer is a biocompatible, noninflammatory, and nonbiodegradable polymer. A non-biodegradable polymer is used in the subject invention to permit localization. Further, if any untoward circumstance should force a physician to take out the implant 12 from a patient, it can be taken out intact. A biodegradable implant will soften and lose its structural integrity over time, making the task of emergency removal difficult, if not impossible.

Drug-loaded EVA matrices are advantageously fabricated by a solvent casting technique. The polymer is first dissolved in an organic solvent, preferably a low boiling solvent such as methylene chloride or chloroform to facilitate eventual removal of the solvent by evaporation. The concentration of the polymer solution advantageously ranges from five to fifteen weight percent. Too dilute a concentration leads to bubble formation during the casting and too concentrated makes it difficult to disperse the drug particles in the solution.

The drug to be embedded in the EVA matrix is dissolved, or in the case a high loading drug level, dispersed in the polymer solution. The drug can be released by permeation through the polymer phase, or if the drug has a low solubility in the polymer, released by diffusion through the pores and channels. As the drug particles near the surface of the matrix are dissolved and released, they leave behind pores and channels through which the embedded drug particles are released. Preferably, the drug particles are sieved, since the size of the drug particles determines the size of the pores and channels. This however is not absolutely necessary unless the drug particles aggregate to form large clumps, for example, several hundred microns in size. Reasonably reproducible release kinetics (i.e., near constant delivery) are obtained with commercially available drug particles which have been micronized.

The polymer solution with drug is then cast into a mold of the desired shape and size. After slow evaporation of the solvent (to prevent bubble formation), the drug molecules or drug particles are embedded in the polymer matrix. The casting is normally done at low temperatures to prevent sedimentation of the drug particles during the solvent evaporation. Typically the polymer solution with drug is poured into a mold that has been cooled to a temperature below the melting point of the solvent. The solution is hence rapidly frozen to allow uniform dispersion of the drug particles in the final matrix.

Other materials suitable for uses as the matrix include silicone rubber, hydrogels such as crosslinked poly(vinyl alcohol) and poly(hydroxy ethylmethacrylate).

Coating

Figure 6:
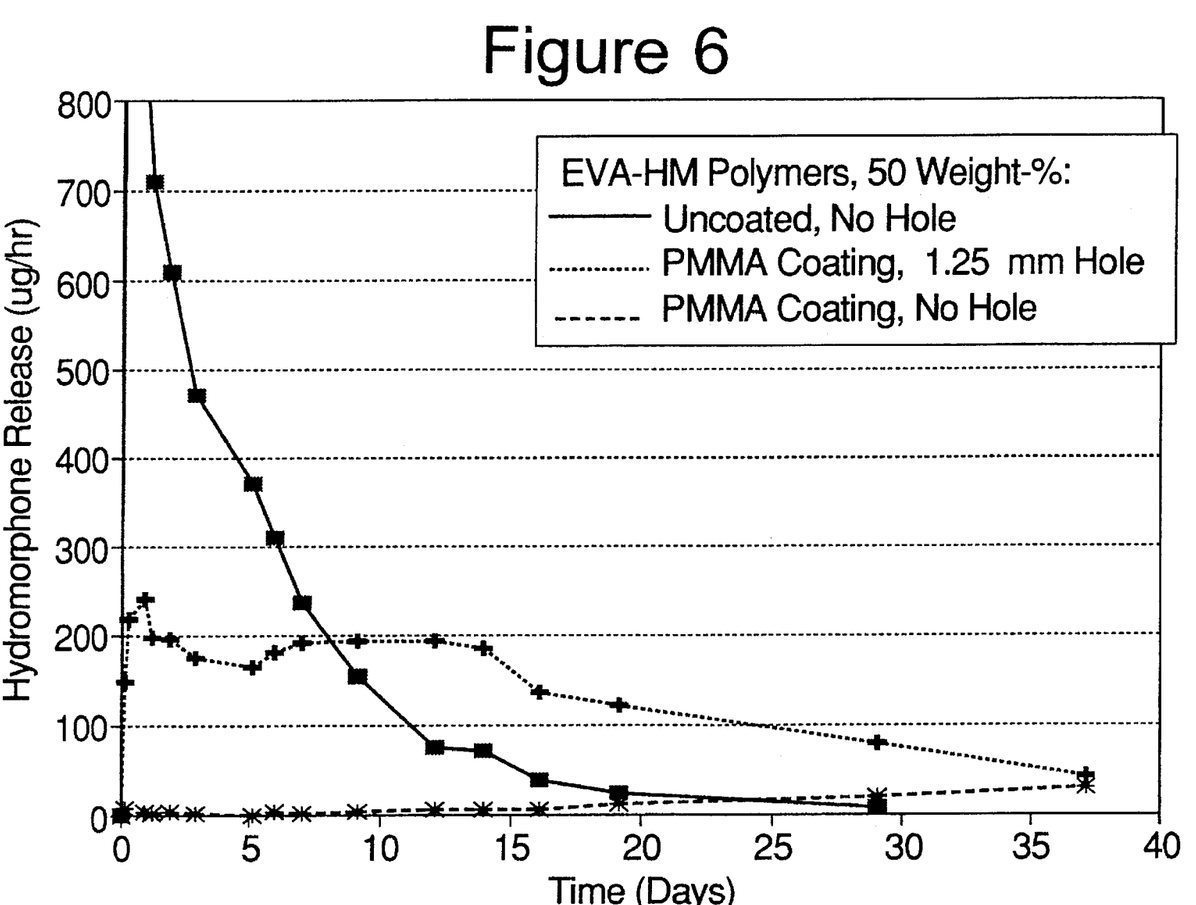
FIG. 6 shows the effects of a poly(methyl methacrylate) coating with and without a central, uncoated, full thickness opening on in vitro hydromorphone release from the device.

Coating the EVA polymer matrix eliminates the potentially deadly "burst effect" normally seen with controlled release devices. An uncoated polymer delivers hydromorphone in a burst or spike within the first two days of drug administration, and then tapers down to a minimum in the ensuing days (see FIG. 6). This is a key problem in using subcutaneous implants for drug delivery, and the subject invention solves the problem for hydromorphone. To eliminate the burst effect and to obtain more steady or constant release kinetics without manipulation of non-uniform drug distribution in the matrix, the EVA polymer containing the drug 14 is coated, except a small opening 10 in the middle, with a coating 12 impermeable to the drug, and tissue biocompatible so as to invoke only minimal fibrous tissue encapsulation of the implant 2. Advantageously, the bone cement poly(methyl methacrylate) is used with hydromorphone. The coating 12 should be thick enough for the intended life of the implant, typically about 100 microns.

Coating of the matrix is advantageously achieved by the dip-coating technique. For example, a coating is applied by impaling the disk on a syringe needle of a chosen diameter and dipping into a polymer solution. After application of several coatings by repeated dip-coating and drying, the needle is removed to expose an uncoated cylindrical aperture. Alternatively, an opening along the axis of the matrix is created after coating the matrix. Drug is released only through this opening. With this configuration, a near constant release of drug is obtained without a drug concentration gradient in EVA polymer.

The coating material is impermeable to hydromorphone, non-biodegradable (negligible cleavage of the polymer backbone or mass loss within a two-month period), and soluble in a solvent that is not a good solvent for the selected matrix. Otherwise, the matrix might partially dissolve during the dip-coating and some of the drug molecules or particles might be embedded in the coating. The solubility parameter of poly(methyl methacrylate) is 9–9.5 $[cal/cm^3]^{0.5}$. Other polymers with this solubility parameter which are impermeable to hydromorphone are suitable coatings for the EVA-hydromorphone polymer.

Drug Loading

The ratio of hydromorphone to EVA polymer is 10–90% by weight hydromorphone, advantageously 30–70%. The drug/EVA mixture is homogeneous. The higher levels of hydromorphone concentration are typically used where the opening 10 is very small (see below).

Implant Geometry

Figure 3:
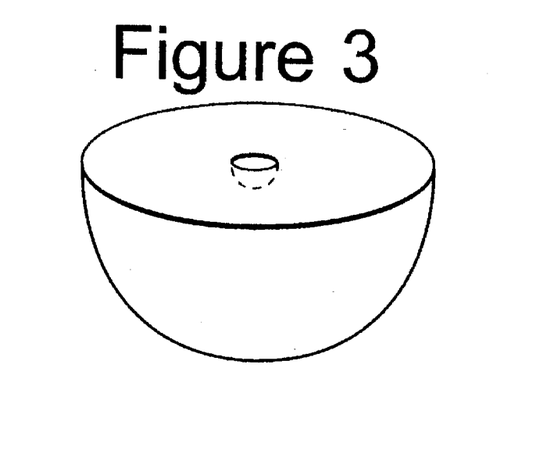
FIG. 3 is a perspective view of the hemisphere embodiment of the invention.
Figure 4:
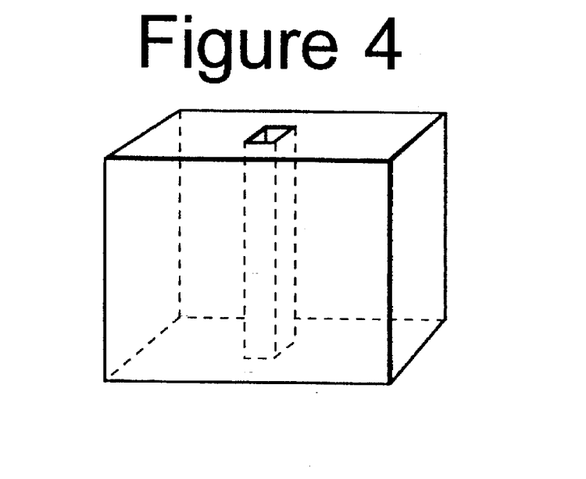
FIG. 4 is a perspective view of the cube embodiment of the invention.

The implant is advantageously cylindrical in shape (see FIGS. 1 and 2). Other geometries where the distance between the uncoated wall and the coated wall (opposite the uncoated wall) remains constant or substantially (±20%) constant throughout the implant, can be used, e.g., a hemisphere where the uncoated wall is in the shape of a hemisphere (FIG. 3), or a cube having a square opening which extends the full height (thickness) of the cube (FIG. 4). These geometries provide a near constant release rate over the life of the implant.

The cylindrical implant is 5–100 mm, advantageously 10–25 mm, in diameter and 1–20 mm, advantageously 1–2 mm in height (thickness).

A single 50 micron–3 mm diameter, advantageously 0.5–1.5 mm diameter, circular or substantially circular opening 10 extends along the axis of the cylindrical device, creating an internal cylindrical uncoated area 16 through which the drug is released. The area of the opening for cylinder, cube, hemisphere or other shape devices, is less than 10%, advantageously less than 1%, of the surface area of the top of the device.

Figure 5:
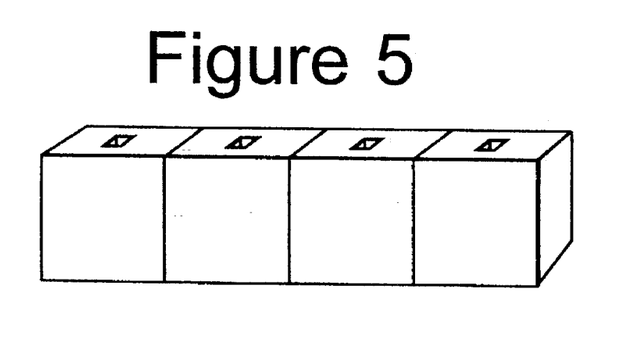
FIG. 5 is a perspective view of the multiunit (tandem) embodiment of the invention.

Multiple unit devices of the invention are formed by juxtaposing cylindrical implants (or other shapes), i.e., where the axes of the individual devices are perpendicular to the axis of the multiple unit device. (See FIG. 5). In the case of a juxtaposed arrangement, the area of contact (i.e., where the units are joined) between individual components (e.g., individual cylinders or cubes) may be coated or uncoated.

In another embodiment, multiple unit devices are formed where the axes of the individual devices (e.g., cylindrical or cubic) are the same as the axis of the multiple unit device. In order to join individual devices in this way and permit release of drug, the individual devices are spaced apart and linked by means of spacers. In one embodiment, the spacers are one or more members running parallel to the multiple unit axis; each of such spacers is attached to the outside wall of each individual device. Alternatively, porous members are alternated between individual devices (and join the devices).

In a further embodiment, small spacers contacting (and joining) the bottom of one individual device and the top of the adjacent device are used to form multiple unit devices. Spacers advantageously are made using the coating material, e.g., poly(methyl methacrylate). In another embodiment, wire coated with the coating material is used as the spacer.

Administration of the Implant

The device of the invention 12 is implanted subcutaneously, advantageously in the upper arm or abdominal areas, using procedures known to those skilled in the art. The dose rate chosen is that which is safe and efficacious for a particular patient. Too low a dose rate results in a lack of pain relief, and too great a dose rate results in sedation followed by respiratory depression. For example, in cancer pain treatment, using a visual analog scale for measuring the pain, and titrating hydromorphone to the patient's subjective level of pain, a disk of appropriate dose rate is chosen for a patient.

Figure 7:
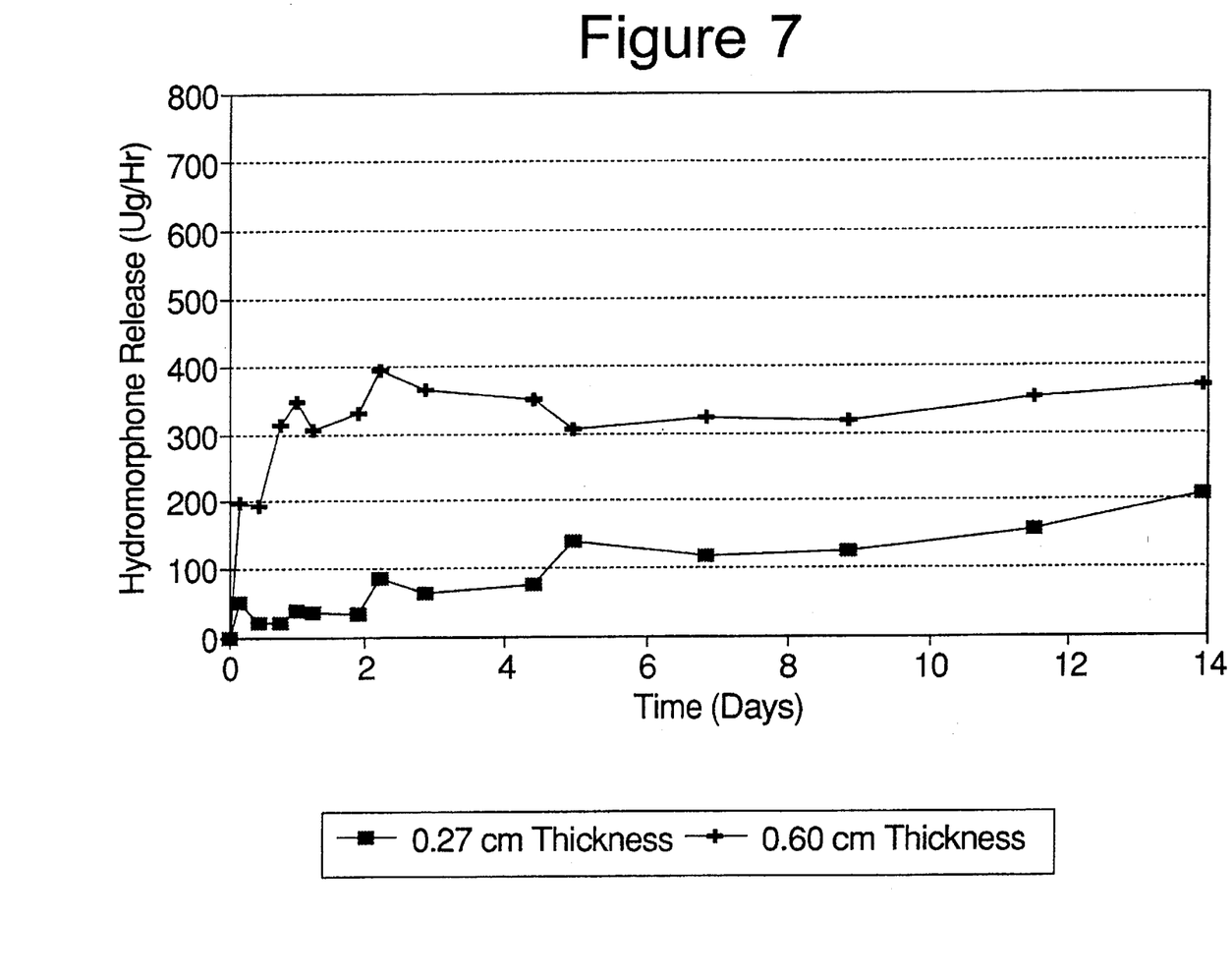
FIG. 7 shows the effect of alterations in the height of the cylindrical device with constant hole and device diameters on in vitro hydromorphone release from the poly(methyl methacrylate)-coated device.
Figure 8:
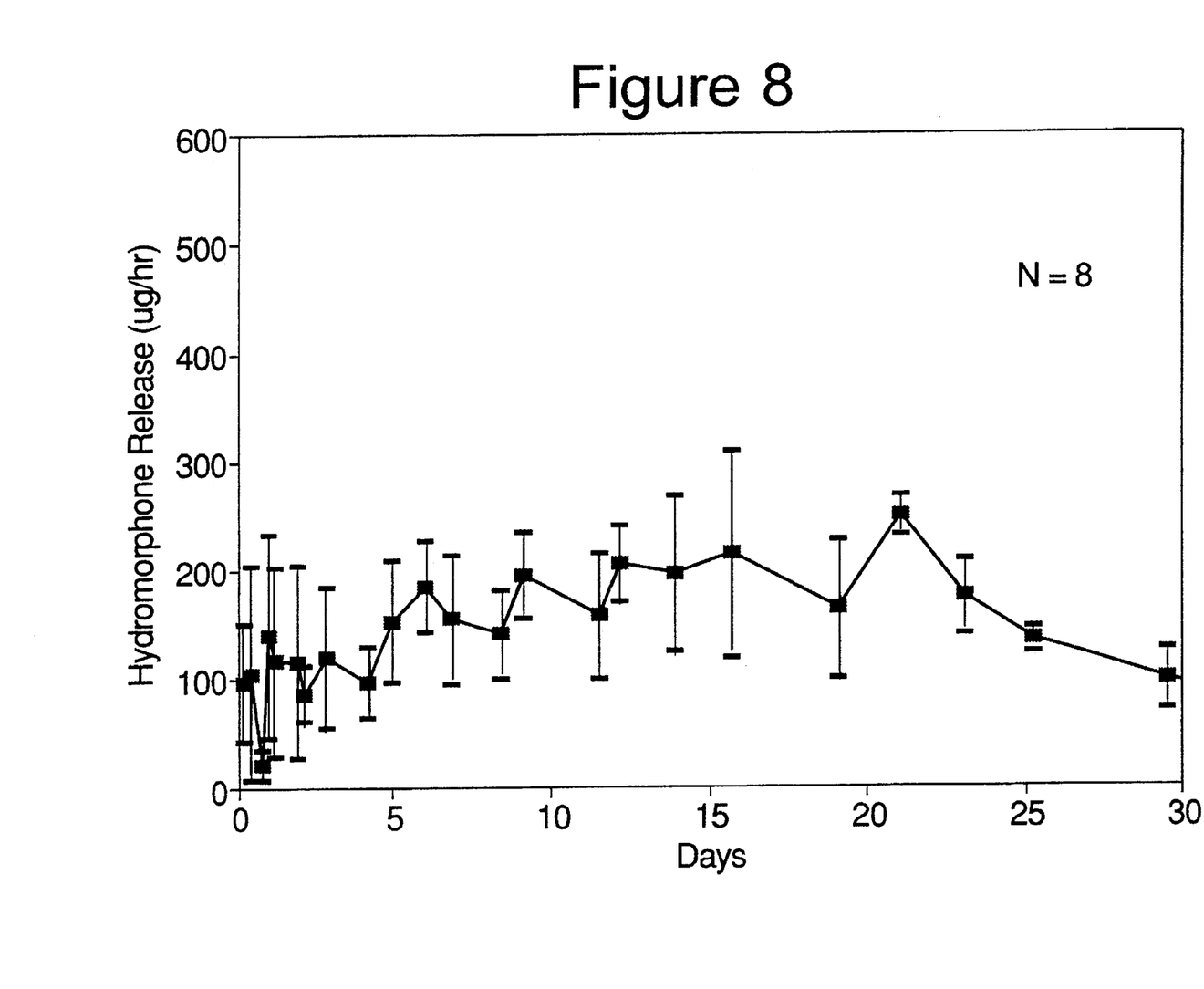
FIG. 8 demonstrates that hydromorphone release from the delivery device of the subject invention exhibited near zero-order kinetics in vitro for up to 4 weeks. The initial release "burst" that complicates many controlled delivery devices was eliminated.

For treatment of cancer pain, implants are typically designed to produce from 0.1–25 mg/hr., advantageously, 0.1 to 10 mg/hr (e.g., 0.25 mg/hr, 1 mg/hr and 4 mg/hr). One to three implants are typically placed in patients. Dose (mg/hr) is advantageously regulated by the height of the cylindrical disk or opening diameter, i.e., increased height or opening diameter means larger release rates (a greater uncoated surface area 16 remains exposed to the external milieu). See FIG. 7. Delivery of multiple implants, either individually or juxtaposed as described above, increases dose rate. Further, increasing drug load increases dose rate.

For treatment of opioid dependence, implants are typically designed to produce 0.1–0.5 mg/hr hydromorphone per hour subcutaneously. For a discussion of methadone maintenance see Strain et al, Ann. Intern. Med. 119, 23–27 (1993), and Gerstein and Lewin, N. Engl. J. Med., 323, 844–848 (1990).

The device can control the release of hydromorphone to desired blood levels for periods of two weeks to in excess of six months. The lifetime of an implant is advantageously regulated by its diameter (increased diameter increases lifetime). Drug loading, opening size and height also have an effect on the lifetime of the implant. An implant lasting four weeks is advantageous for cancer pain treatment since an oncologist will usually evaluate his cancer patient with chronic pain at least once a month. The degree of pain may increase due to a progressive tumor necessitating a higher dose. Moreover, there is tolerance to hydromorphone such that higher doses may be needed to control the same degree of pain in the succeeding month.

The device of the subject invention provides near constant delivery of hydromorphone. "Near constant" is defined as ± a 5 fold (500%), advantageously ± a two fold (200%) variation, most advantageously ± single fold (100%) variation in the target delivery rate (in vivo or in vitro). A greater than 5 fold variation results in a "burst effect" which could cause damage or even death to the recipient.

In one embodiment of the invention, the drug release from the implant is supplemented with additional delivery (oral, rectal etc.) of an opiate when the patient is experiencing heightened pain.

Treatment of Pain

The implant of the invention can be used in any case where oral opiates are indicated. In about 85% of patients with cancer pain, oral opiates are indicated. The invention is particularly advantageous where oral administration is not appropriate or available or where there is toxicity from intermittent administration. The implant of the invention has application in the treatment of cancer pain in humans or in other animals. The implant has utility in the treatment of other types of chronic pain such as chronic severe pain resulting from degenerative musculoskeletal or nervous system diseases.

Treatment of Opioid Dependence

The implant of the invention is useful in the treatment of opioid drug (e.g., heroin) addiction. Hydromorphone given in low dosages over extended periods of time is effective in the treatment of drug addiction. The implant of the invention can be used in any situation where a methadone maintenance program could be used. The implant insures that low dose rates of the drug can be sustained for extended periods without dependence on patient compliance with oral dose schedules. Further use of the implant provides drug in a form which virtually eliminates the possibility of illicit use.

The following Examples are illustrative, but not limiting of the compositions and methods of the present invention. Other suitable modifications and adaptations of a variety of conditions and parameters normally encountered in clinical therapy which are obvious to those skilled in the art are within the spirit and scope of this invention.

EXAMPLES

Example 1

Polymer Formulation

A low temperature solvent casting technique was used to formulate the hydromorphone implants used in these experiments. EVA (MW about 50,000) (Elvax-40W, Dupont) with 40% by weight of vinyl acetate, was cleaned in water and dissolved in methylene chloride ($CH_2Cl_2$) to produce a 10% solution. The polymer can be purified by extraction with distilled water in a Soxhlet extractor for three days, followed by extraction with acetone for another four days to remove impurities and anti-oxidants. The hydromorphone-incorporated matrices were prepared by solvent casting. A 10% (w/v) solution of EVA was made by dissolving 2 gm of pure EVA in 20 ml of methylene chloride.

Non-sieved hydromorphone hydrochloride powder (Knoll Pharmaceuticals) was added at room temperature to the 10% EVA to produce a 50 weight-percent solution which was then magnetically stirred for approximately 10 minutes. Hydromorphone powder can be mechanically sieved to a predetermined range of particle size and suspended in the EVA solution. Any visible macroscopic clumps remaining in this solution were broken apart with a glass stirring rod.

The homogeneous suspension was quickly poured into a recrystallization dish 14 cm in diameter prechilled to −78° C. on dry ice. The dish was covered to minimize condensation. After solidification, which occurred within 15 minutes, the sample was dried in two 48-hour stages: first at −20° C., and then under vacuum at room temperature.

Hydromorphone polymer disks were cut from the dried circular slab with a number 7 cork borer to yield approximately 15 polymers of about 0.27 cm thickness and 1.05 cm diameter. For those experiments designed to demonstrate flexibility in the amount of hydromorphone released per hour, double and triple thickness polymers were prepared (0.55–0.65 cm and 0.83 cm thick, respectively) by doubling or tripling the amount of EVA-hydromorphone mixture placed in the mold. Polymers of 2.13 cm diameter were also cut from the dried EVA-hydromorphone slab using a number 15 cork borer to demonstrate flexibility in duration of drug release.

Example 2

Polymer Coating

Prior to coating, an 18 gauge hollow steel needle was passed through the full thickness of each EVA-hydromorphone polymer at approximately the center of the circular face of the polymer. Each polymer was then "dip-coated" in a 10% poly(methyl methacrylate) (MW about 996,000) (Aldrich) solution in acetone for 10 seconds. The poly(methyl methacrylate) coating was allowed to air dry at room temperature for 24 hours at which time the needle was removed, the polymer was turned over, and the needle was passed back through the central hole in the polymer in the opposite direction. This procedure was then repeated two additional times to produce a triple thickness impermeable coating of poly(methyl methacrylate) that fully encased each polymer with the exception of an 18 gauge cylinder (about 1.25 mm diameter) passing through the center of each polymer, much like a button hole in a button. The coating thickness was about 100–200 µm. The solubility parameter of the coating material is 9–9.5 $[cal/cm^3]^{0.5}$.

Example 3

In Vitro Release Assay

Hydromorphone release from the coated EVA-hydromorphone polymers was assessed in vitro by placing each polymer in a glass scintillation vial containing 10 ml of pH 7.4 0.1M sodium phosphate buffer warmed to 37° C. All vials were placed in a water bath at 37° C. At appropriate intervals, the buffer in each vial was collected and stored in centrifuge tubes at about 4° C. and 10 ml of fresh phosphate buffer at 37° C. was added back to each vial. Samples were periodically assayed in bulk on a UV spectrophotometer at 254 nm in matched cuvettes zeroed against blank 0.1M pH 7.4 phosphate buffer. Hydromorphone standards were included in each assay and, when necessary, samples were diluted in buffer such that their absorbance could be measured on the linear part of the standard curve.

Figure 9:
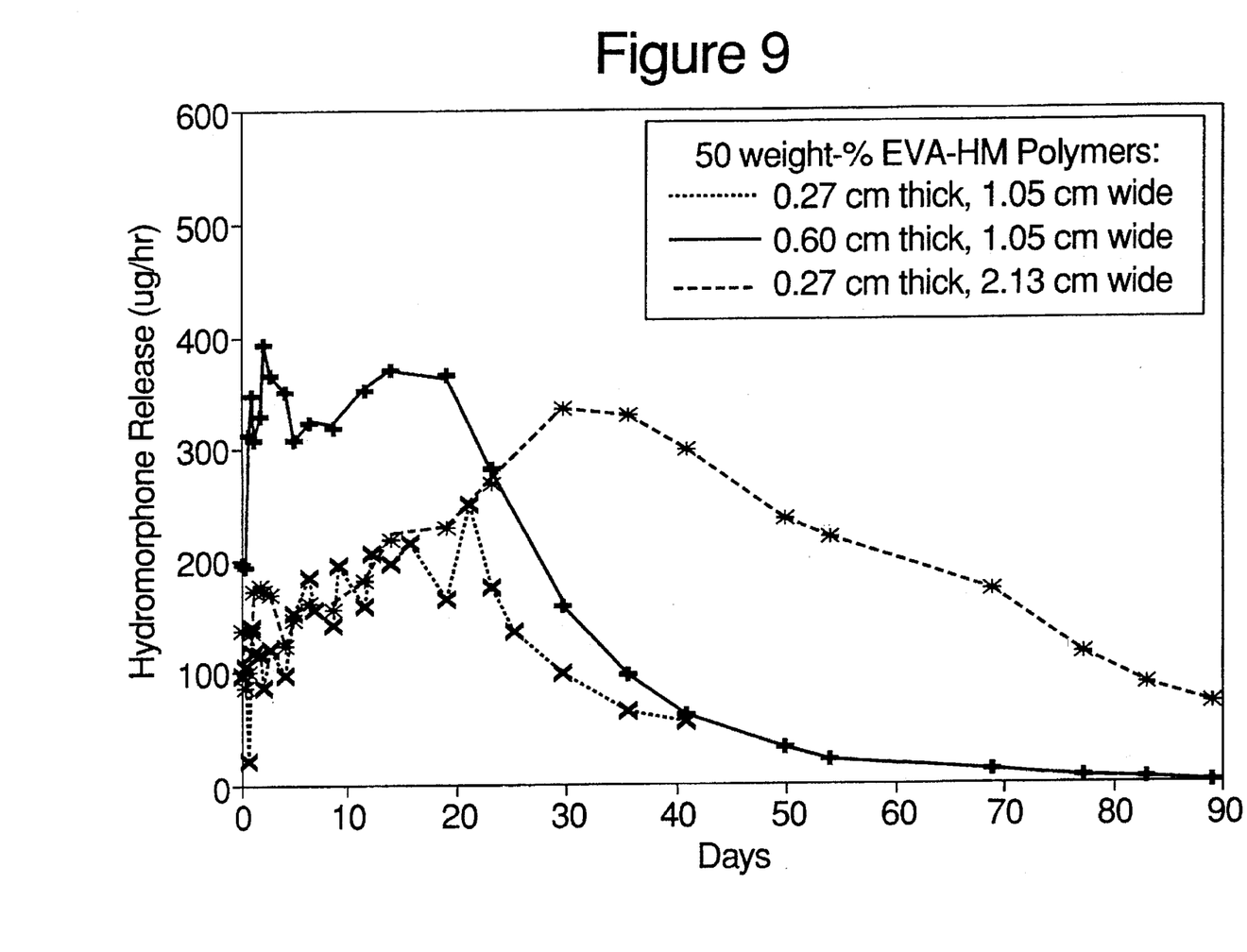
FIG. 9 shows that flexibility in the amount of hydromorphone released per hour and the duration of hydromorphone delivery in vitro was easily achieved through simple modifications of the delivery devices.

The coated EVA-hydromorphone polymers released hydromorphone at a constant mean rate of 164 µg/hr beginning 4 days after in vitro release and continuing for over 4 weeks. Coating these polymers with an impermeable layer of poly(methyl methacrylate) except for the central full thickness hole eliminated the initial "burst" that complicates many other controlled delivery devices. Flexibility in the amount of hydromorphone delivered per hour and the duration of drug delivery was easily achieved by varying the thickness and diameter of the coated EVA-hydromorphone polymers. See FIG. 9.

In Vivo Experiments

Example 4A

Polymer Release

Under general anesthesia, two coated EVA-hydromorphone polymers were placed in a subcutaneous pocket in each of five adult rabbits. Rabbits were housed one to a cage and fed rabbit chow and water ad libitum. Blood samples were drawn from each animal prior to implantation and at appropriate intervals thereafter for up to 6 weeks after placement. Blood samples were centrifuged and plasma was removed and stored in a freezer at −20° C. Plasma samples were assayed in bulk using a commercially available radio-immunoassay opiate screen and hydromorphone standards. In an attempt to demonstrate a relationship between the amount of hydromorphone implanted and the resultant plasma drug levels, two additional rabbits each had 3 sets of 2 polymers sequentially implanted at approximately one week intervals. The previously implanted coated polymers were left in place so that the rabbits had 2 then 4 then 6 polymers delivering hydromorphone at the same time. Blood was removed and plasma was assayed as described above.

Figure 10:
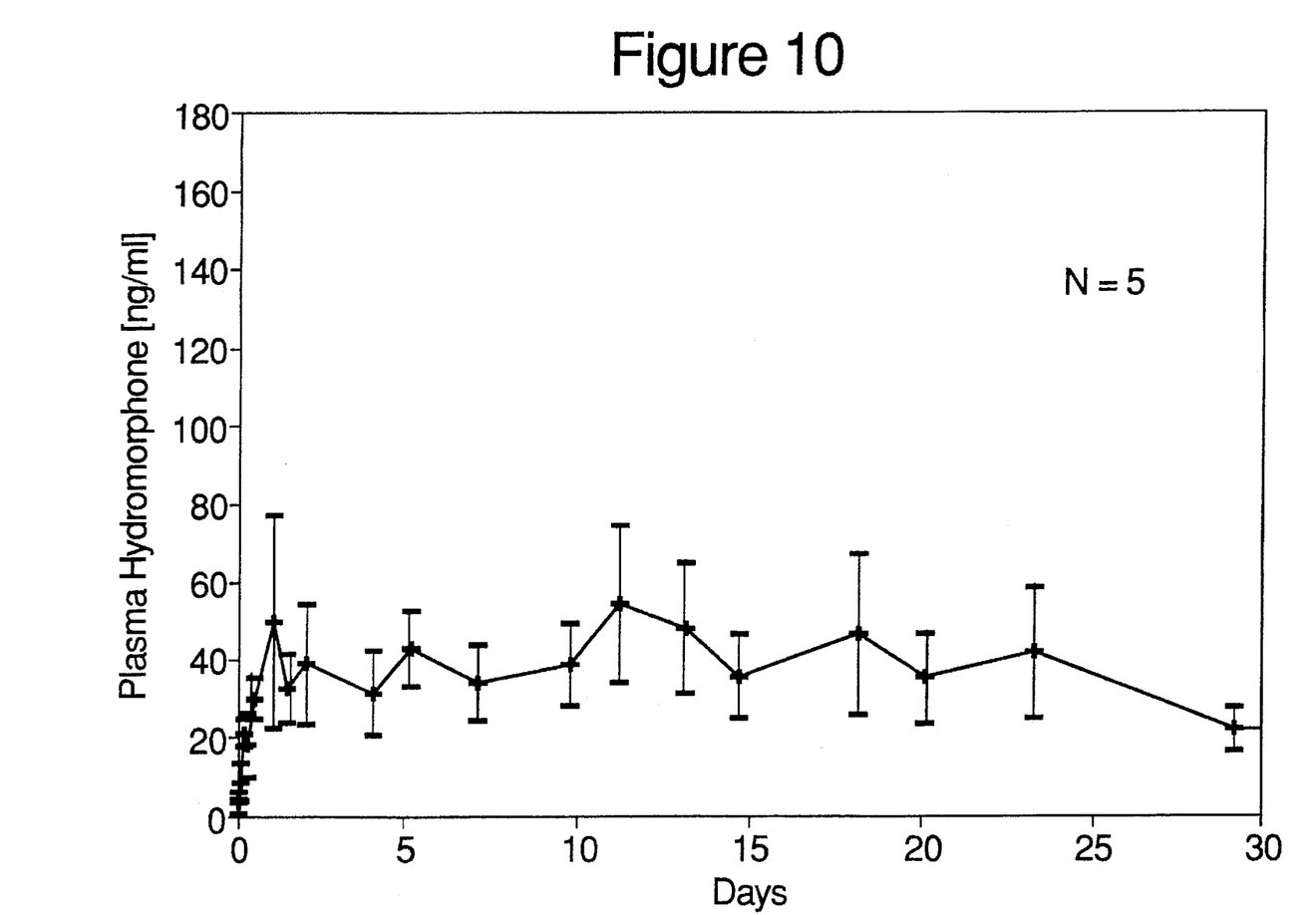
FIG. 10 shows that 2 delivery devices placed subcutaneously in each of 5 rabbits produced stable, sustained plasma hydromorphone concentrations for up to 4 weeks. These plasma concentrations were within the human therapeutic range.
Figure 11:
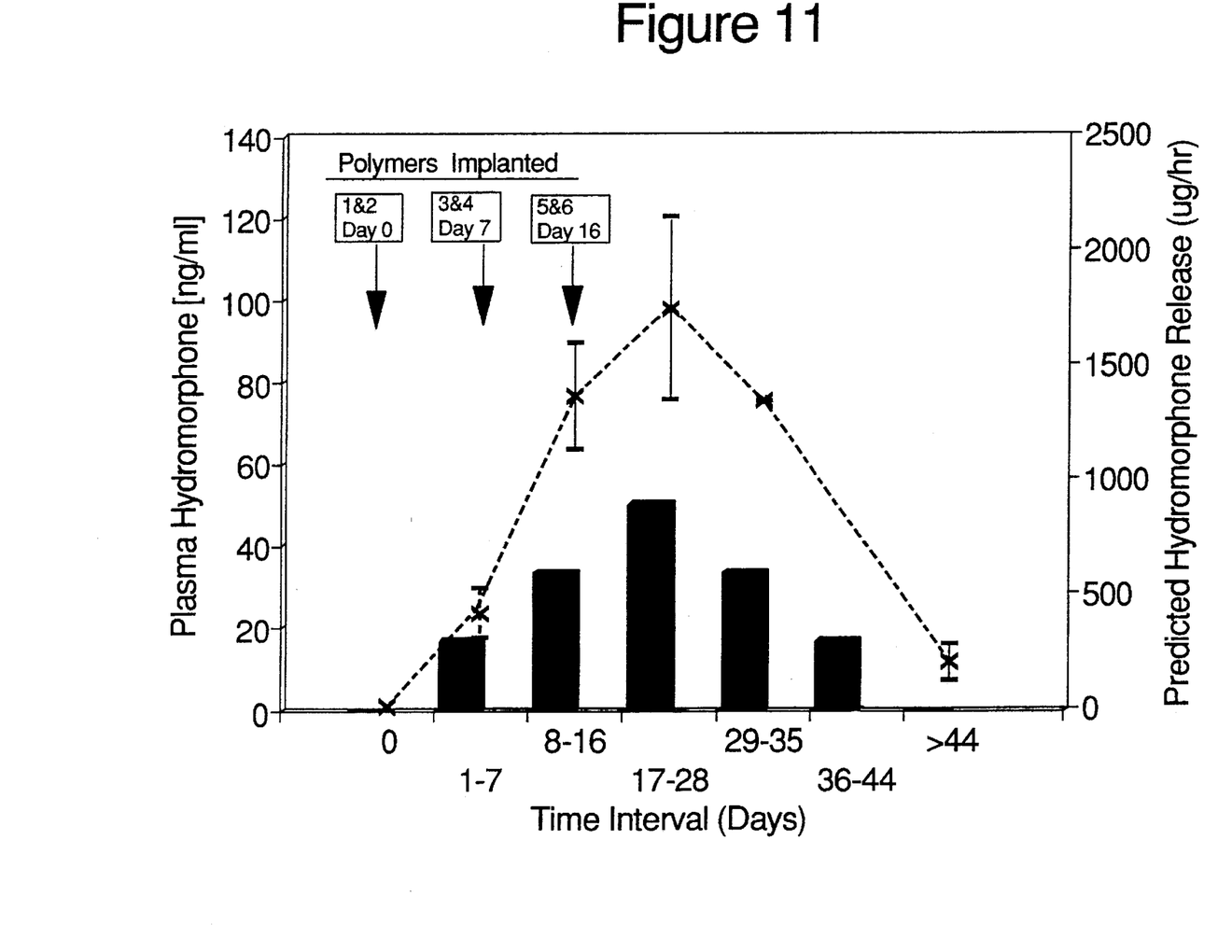
FIG. 11 shows the predicted hydromorphone release from multiple implanted delivery devices and the observed plasma hydromorphone concentrations in rabbits over time. Increasing the number of subcutaneously implanted delivery devices produced a sustained and predictable increase in rabbit plasma hydromorphone concentrations. Systemic toxicity with 6 implants (approximately 900 μg/hr hydromorphone) was limited to transiently increased sedation and decreased oral intake.

Two devices placed subcutaneously in rabbits produced stable and sustained plasma hydromorphone levels of 23–37 ng/ml for up to 4 weeks (see FIG. 10). Increasing the number of subcutaneous implants in an individual rabbit produced a sustained and predictable increase in that rabbit's plasma hydromorphone concentration (see FIG. 11). No significant toxicity was observed in these animal experiments with the exception of mild transient sedation after the implantation of 2 devices and increased sedation with decreased oral intake after the implantation of larger numbers of devices that also appeared to be transient.

Example 4B

Osmotic Pump Release

In order to validate the rabbit plasma hydromorphone levels measured after device implantation, Alzet osmotic pumps were prepared that delivered approximately the same amount of hydromorphone per hour as two devices of the invention. Under general anesthesia, an Alzet osmotic pump (mean pumping rate=2.08µl/hr, mean fill volume=2073 µl) was placed subcutaneously in each of 4 rabbits and blood samples were collected as described above. Plasma was also prepared and analyzed as described above.

Figure 12:
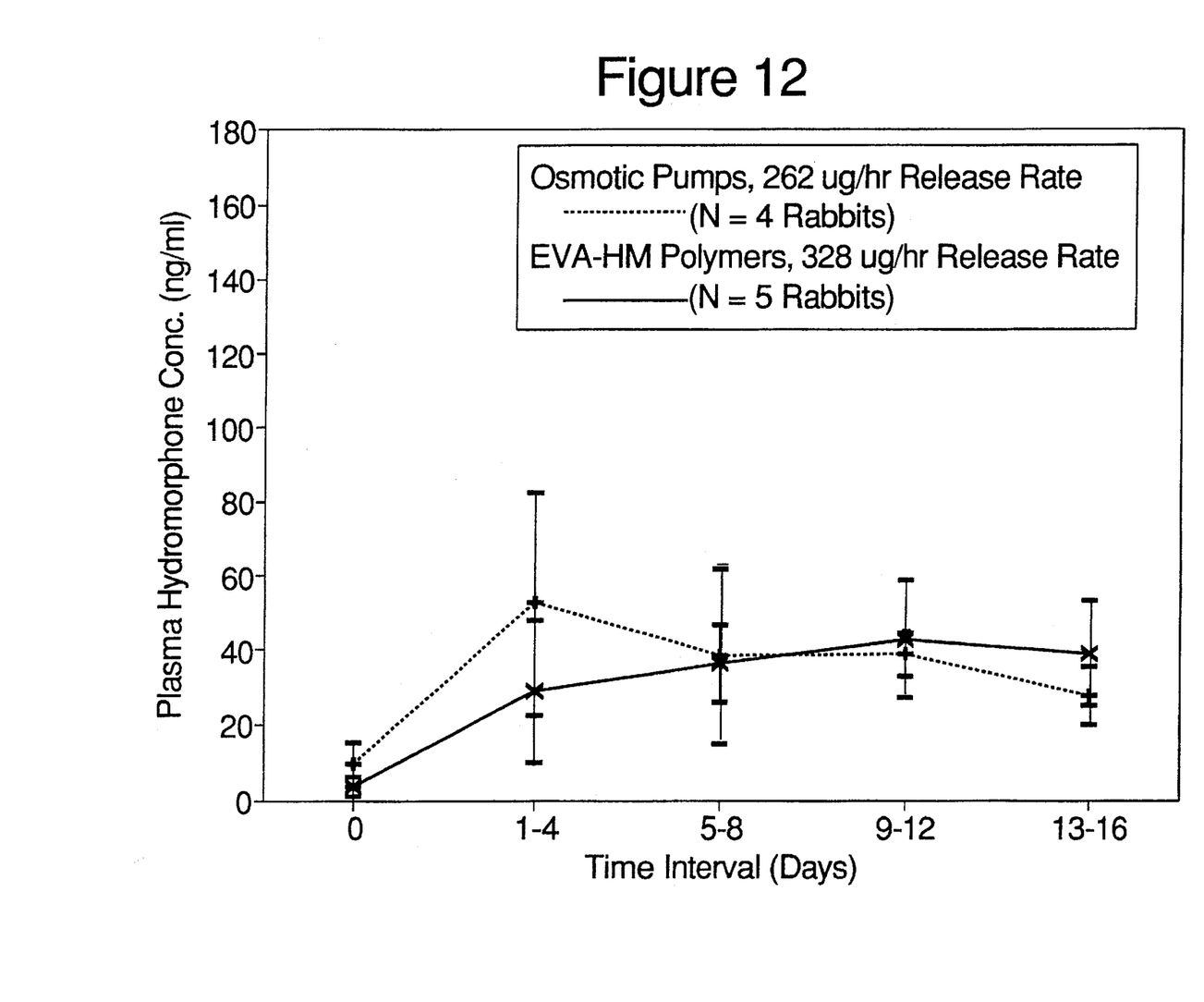
FIG. 12 shows that subcutaneously implanted osmotic pumps that delivered approximately the same amount of hydromorphone per hour as two delivery devices of the invention, produced comparable rabbit plasma hydromorphone concentrations.

Alzet osmotic pumps that are designed to deliver 297 µg/hr of hydromorphone produced mean rabbit plasma hydromorphone levels 28 to 51 ng/ml over a 2 week period (see FIG. 12).

Example 4C

Hydromorphone Intravenous Boluses

Single 600 µg and 1200 µg boluses (equal to ½ to 1 times the cumulative amount delivered subcutaneously by polymers or pumps over 4 hours, a typical dosing interval in humans) were administered intravenously to two additional rabbits and samples were collected at 0,1,2,5,10,20,30,45, 60,90,120,150,180,210 and 240 minutes.

Figure 13:
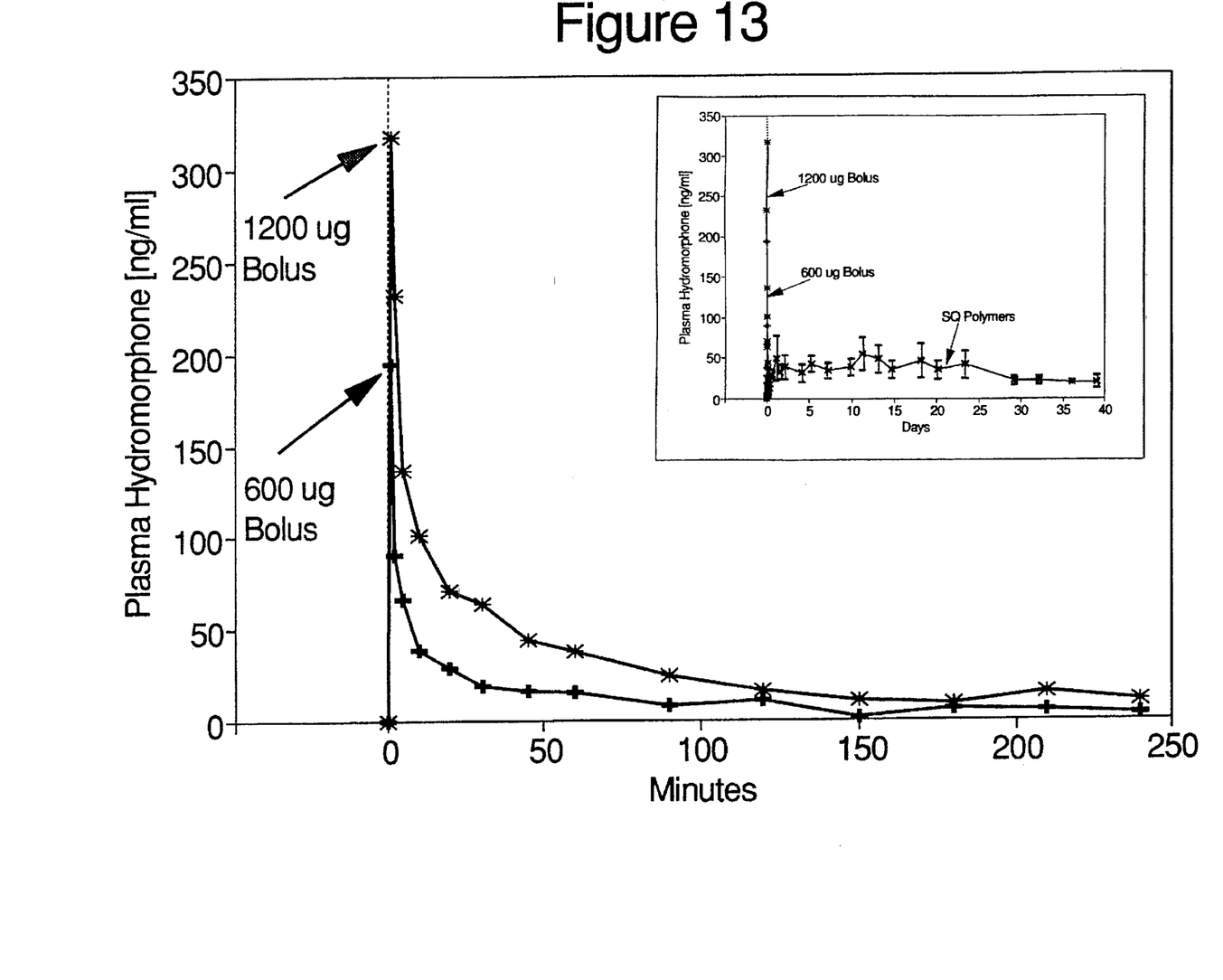
FIG. 13 shows an intravenous bolus equal to 50% (600 μg) and 100% (1200 μg) of the cumulative amount of hydromorphone released by two delivery devices over 4 hours (a typical human dosing interval) produced peak rabbit plasma concentrations within one minute followed by a rapid fall to baseline over several hours. Peak plasma hydromorphone concentrations were well tolerated and at least 4 times higher than the steady-state concentration obtained with the device of the invention.

Six hundred and 1200 µg hydromorphone boluses produced peak rabbit plasma hydromorphone levels of almost 200 and over 250 ng/ml at one minute with a rapid fall back to baseline by 4 hours (see FIG. 13).

It will be readily apparent to those skilled in the art that numerous modifications and additions may be made to both the present invention, the disclosed device, and the related system without departing from the invention disclosed.

What is claimed is:

1. A method of providing prolonged relief of pain in a mammal suffering from pain comprising subcutaneously administering a delivery system comprising:

i) a matrix comprising poly(ethylene-vinyl acetate), ii) hydromorphone embedded homogeneously in said matrix, iii) poly(methyl methacrylate) coating said matrix, wherein said delivery system is adapted to deliver said hydromorphone at a rate of plus or minus 500% of the target delivery rate, to said mammal, and wherein said delivery system has a geometry such that there is an external coated wall and an internal uncoated wall and the distance between the uncoated wall and the coated wall opposite the uncoated wall is substantially constant throughout the delivery system.

2. A method as in claim 1 wherein said delivery system is cylindrical in shape and has a cylindrical shaped opening along the axis of said delivery system forming an internal wall in said delivery system.

3. A method as in claim 1 wherein the thickness of said coating is 0.1–1 min.

4. A method as in claim 1 wherein said matrix contains 50% by weight hydromorphone and 50% by weight poly (ethylene-vinyl acetate).

5. A method as in claim 2 wherein the length of the delivery system along its axis is 1–20 mm and the diameter of the delivery system is 5–100 mm.

6. A method as in claim 2 wherein said cylindrical shaped opening has a diameter of 0.05–3 mm.

7. A method as in claim 1 wherein said pain is cancer pain.

8. A method as in claim 1 wherein said delivery system is adapted to deliver said hydromorphone at a rate of plus or minus 200% of the target delivery rate.

9. A method as in claim 1 wherein said delivery system is adapted to deliver said hydromorphone at a rate of plus or minus 100% of the target delivery rate.

10. A method as in claim 1 wherein the distance between the uncoated wall and the coated wall opposite the uncoated wall varies by no more than plus or minus 20%.

11. A method of providing prolonged relief of pain in a mammal suffering from pain comprising subcutaneously administering a delivery system comprising:

i) a matrix comprising polyethylene vinyl (acetate), ii) hydromorphone embedded homogeneously in said matrix, and iii) a poly(methyl methacrylate) coating surrounding said matrix wherein said delivery system is cylindrical in shape and has a cylindrical shaped opening along the axis of said delivery system forming an internal uncoated wall in said delivery system, to said mammal.

12. A method as in claim 11 wherein the thickness of said coating is 0.1–1 min.

13. A method as in claim 11 wherein said matrix contains 50% by weight hydromorphone and 50% by weight poly (ethylene-vinyl acetate).

14. A method as in claim 13 wherein said hydromorphone is homogeneously distributed in said matrix.

15. A method as in claim 11 wherein the length of the delivery system along its axis is 1–20 mm and the diameter of the delivery system is 5–100 mm.

* * * * *